US006976973B1

(12) United States Patent
Ruddell et al.

(10) Patent No.: US 6,976,973 B1
(45) Date of Patent: Dec. 20, 2005

(54) PERITONEAL DIALYSIS CATHETERS

(75) Inventors: Scott A. Ruddell, Waukegan, IL (US);
Atif Yardimci, Northbrook, IL (US);
Jorge Del Castillo, Des Plaines, IL (US)

(73) Assignee: Baxter International Inc., Deerfield, IL (US)

( * ) Notice: Subject to any disclaimer, the term of this patent is extended or adjusted under 35 U.S.C. 154(b) by 139 days.

(21) Appl. No.: 09/689,508

(22) Filed: Oct. 12, 2000

(51) Int. Cl.$^7$ ................................................ A61M 1/00
(52) U.S. Cl. ...................... 604/29; 604/93.01; 604/264
(58) Field of Search ............................. 604/29–35, 20, 604/27, 93.01, 164.01, 264, 544, 317, 8, 604/19, 36, 39, 40, 94.01, 131, 164.11, 523, 604/540

(56) References Cited

U.S. PATENT DOCUMENTS

| | | | |
|---|---|---|---|
| 3,707,967 | A | 1/1973 | Kitrilakis et al. |
| 4,184,497 | A | 1/1980 | Kolff et al. |
| 4,239,041 | A | 12/1980 | Popovich et al. |
| 4,306,976 | A | 12/1981 | Bazzato |
| 4,351,333 | A | 9/1982 | Lazarus et al. |
| 4,368,737 | A | 1/1983 | Ash |
| 4,381,003 | A | 4/1983 | Buoncristiani |
| 4,396,382 | A | 8/1983 | Goldhaber |
| 4,398,910 | A | 8/1983 | Blake et al. |
| D272,651 | S | 2/1984 | Mahurkar |
| 4,465,481 | A | 8/1984 | Blake |
| 4,490,137 | A | 12/1984 | Moukheibir |
| 4,496,349 | A | 1/1985 | Cosentino |
| 4,498,902 | A | 2/1985 | Ash et al. |
| 4,543,087 | A * | 9/1985 | Sommercorn et al. ........ 604/43 |
| 4,581,012 | A | 4/1986 | Brown et al. |
| 4,586,920 | A | 5/1986 | Peabody |
| 4,687,471 | A | 8/1987 | Twardowski et al. |

(Continued)

FOREIGN PATENT DOCUMENTS

DE 35 22 782 1/1987

(Continued)

OTHER PUBLICATIONS

Lange, et al., "Automatic Continuous High Flow Rate Peritoneal Dialysis," Renal Service and Laboratory, Dept. of Medicine and Pediatrics, New York Medical College, vol. XIII Trans. Amer. Soc. Artif. Int. Organs, 1967, pp. 164-167.

*Primary Examiner*—James Housel
*Assistant Examiner*—Ann Lam
(74) *Attorney, Agent, or Firm*—Joseph P. Reagen; Bell, Boyd & Lloyd LLC

(57) ABSTRACT

A catheter suitable for use in performing peritoneal dialysis. The catheter is a dual lumen catheter which allows for continuous flow peritoneal dialysis. Dialysate flows through the catheter into the patient via one lumen and simultaneously flows through the catheter out of the patient via the second lumen. The dual lumen dialysis catheter has a flexible tube which has an implantable portion extending from an external patient portion. Both of the lumens have openings in the external patient portion for connecting to a supply and drain of dialysate, respectively. The implantable portion has a preformed curved segment which has an outlet for the first lumen to flow dialysate into the patient's peritoneal cavity. The implantable portion has an opening for the second lumen at the distal end to flow dialysate out of the peritoneal cavity and removal from the patient. The catheter facilitates mixing of fresh and spent dialysate inside the peritoneal cavity by inflowing fresh dialysate into the cavity at a location substantially separated from the cavity outflow location, and by directing the inflow of dialysate into the cavity opposite the cavity outflow location.

44 Claims, 6 Drawing Sheets

U.S. PATENT DOCUMENTS

| | | | |
|---|---|---|---|
| 4,772,269 A | 9/1988 | Twardowski et al. | |
| 4,832,054 A | 5/1989 | Bark | |
| 4,895,561 A | 1/1990 | Mahurkar | |
| 5,037,385 A | 8/1991 | O'Byrne | |
| 5,053,023 A | 10/1991 | Martin | |
| 5,057,073 A | 10/1991 | Martin | |
| 5,057,075 A * | 10/1991 | Moncrief et al. | 604/49 |
| 5,098,413 A | 3/1992 | Trudell et al. | |
| 5,106,368 A | 4/1992 | Uldall et al. | |
| 5,188,593 A * | 2/1993 | Martin | 604/43 |
| 5,197,951 A | 3/1993 | Mahurkar | |
| 5,207,650 A | 5/1993 | Martin | |
| 5,209,723 A | 5/1993 | Twardowski et al. | |
| 5,221,255 A | 6/1993 | Mahurkar et al. | |
| 5,221,256 A | 6/1993 | Mahurkar | |
| 5,250,041 A | 10/1993 | Folden et al. | |
| 5,254,084 A | 10/1993 | Geary | |
| 5,322,519 A | 6/1994 | Ash | |
| 5,334,139 A | 8/1994 | Jeppsson et al. | |
| 5,338,293 A | 8/1994 | Jeppsson et al. | |
| 5,346,471 A * | 9/1994 | Raulerson | 604/43 |
| 5,350,358 A | 9/1994 | Martin | |
| 5,364,344 A | 11/1994 | Beattie et al. | |
| 5,378,230 A | 1/1995 | Mahurkar | |
| 5,380,276 A | 1/1995 | Miller | |
| 5,380,298 A * | 1/1995 | Zabetakis et al. | 604/265 |
| 5,421,814 A | 6/1995 | Geary | |
| 5,423,768 A | 6/1995 | Folden et al. | |
| 5,464,398 A | 11/1995 | Haindl | |
| 5,480,392 A * | 1/1996 | Mous | 604/280 |
| 5,509,897 A | 4/1996 | Twardowski et al. | |
| 5,527,274 A * | 6/1996 | Zakko | 604/28 |
| 5,569,182 A | 10/1996 | Twardowski et al. | |
| 5,683,640 A * | 11/1997 | Miller et al. | 264/255 |
| 5,685,867 A | 11/1997 | Twardowski et al. | |
| 5,718,692 A | 2/1998 | Schon et al. | |
| 5,776,111 A | 7/1998 | Tesio | |
| 5,788,680 A | 8/1998 | Linder | |
| 5,795,326 A | 8/1998 | Simán | |
| 5,807,311 A | 9/1998 | Palestrant | |
| 5,807,329 A * | 9/1998 | Gelman | 604/102.03 |
| 5,931,829 A | 8/1999 | Burbank et al. | |
| 5,947,953 A | 9/1999 | Ash et al. | |
| 5,961,486 A | 10/1999 | Twardowski et al. | |
| 5,964,796 A | 10/1999 | Imran | |
| 5,968,009 A | 10/1999 | Simán | |
| 5,976,103 A | 11/1999 | Martin | |
| 5,989,206 A | 11/1999 | Prosl et al. | |
| 5,989,213 A | 11/1999 | Maginot | |
| 6,001,079 A | 12/1999 | Pourchez | |
| 6,048,329 A | 4/2000 | Thompson et al. | |
| 6,074,374 A | 6/2000 | Fulton | |
| 6,117,106 A | 9/2000 | Wasicek et al. | |
| 6,126,631 A | 10/2000 | Loggie | |
| 6,132,405 A | 10/2000 | Nilsson et al. | |
| 6,146,354 A | 11/2000 | Beil | |
| 6,156,016 A | 12/2000 | Maginot | |
| 6,159,195 A | 12/2000 | Ha et al. | |
| 6,190,349 B1 | 2/2001 | Ash et al. | |
| 6,190,371 B1 | 2/2001 | Maginot et al. | |
| 6,193,684 B1 | 2/2001 | Burbank et al. | |
| 6,206,849 B1 | 3/2001 | Martin et al. | |
| 6,234,991 B1 | 5/2001 | Gorsuch | |
| 6,245,039 B1 | 6/2001 | Brugger et al. | |
| 6,248,092 B1 | 6/2001 | Miraki et al. | |
| 6,258,079 B1 | 7/2001 | Burbank et al. | |
| 6,280,423 B1 | 8/2001 | Davey et al. | |
| 6,290,669 B1 | 9/2001 | Zicherman | |
| 6,302,875 B1 | 10/2001 | Makower et al. | |
| 6,497,676 B1 * | 12/2002 | Childers et al. | 604/29 |
| 6,656,146 B1 * | 12/2003 | Clayman et al. | 604/8 |
| 2001/0014793 A1 | 8/2001 | Brugger et al. | |

FOREIGN PATENT DOCUMENTS

| | | |
|---|---|---|
| DE | 3739556 | 6/1989 |
| EP | 0 333 308 | 9/1989 |
| EP | 0 333 308 B1 | 9/1989 |
| EP | 0 381 042 | 8/1990 |
| EP | 0 381 042 A1 | 8/1990 |
| EP | 0 504 934 | 9/1992 |
| EP | 0 504 934 B1 | 9/1992 |
| EP | 0 509 715 A1 | 10/1992 |
| EP | 0 535 874 | 4/1993 |
| EP | 0 535 874 B1 | 4/1993 |
| EP | 0 554 722 | 8/1993 |
| EP | 0 554 722 A1 | 8/1993 |
| EP | 0 684 845 | 12/1995 |
| EP | 0 684 845 B1 | 12/1995 |
| EP | 1 110 564 A2 | 6/2001 |
| EP | 1 110 565 A2 | 6/2001 |
| GB | 2 245 496 | 1/1992 |
| WO | WO 88/03389 | 5/1988 |
| WO | WO 97/37699 | 10/1997 |
| WO | WO 98/17333 | 4/1998 |
| WO | WO 98/50088 | 11/1998 |
| WO | WO 99/07301 | 2/1999 |
| WO | WO 00/10385 | 3/2000 |
| WO | WO 00/20050 | 4/2000 |
| WO | WO 01/58509 A1 | 8/2001 |

* cited by examiner

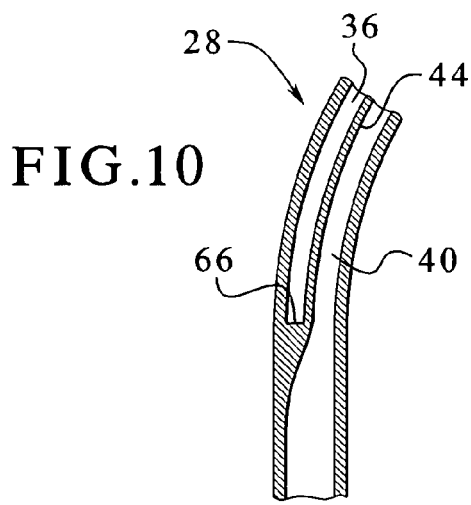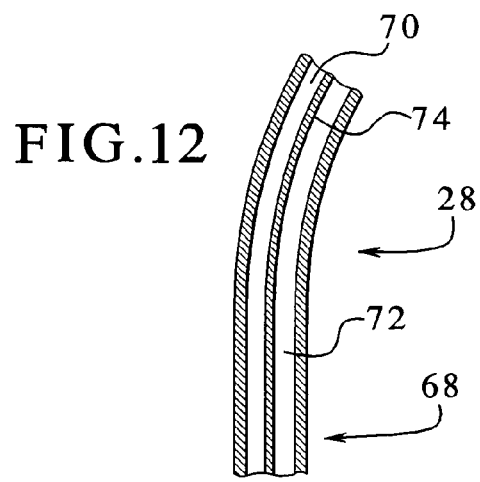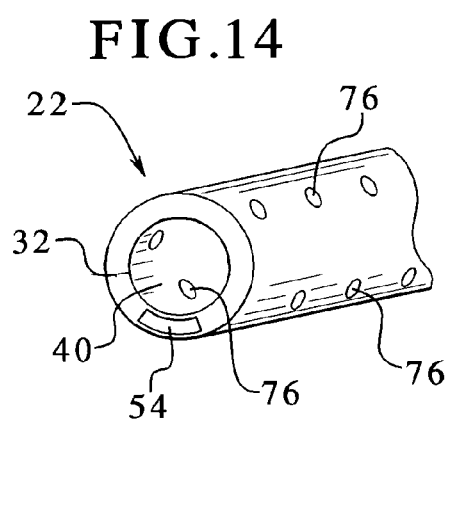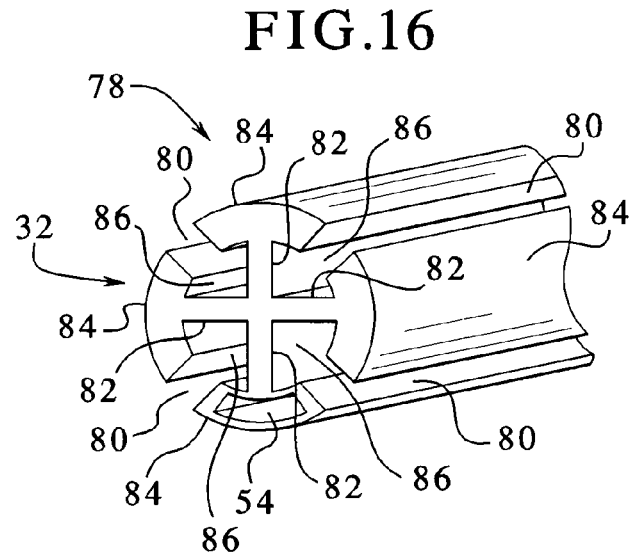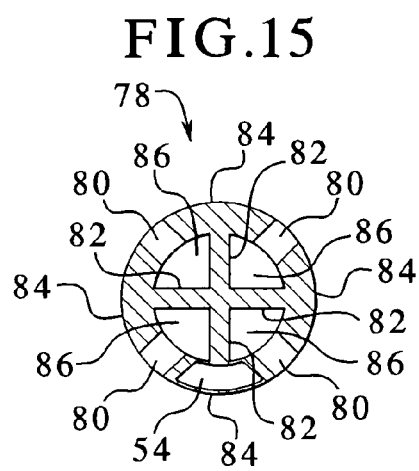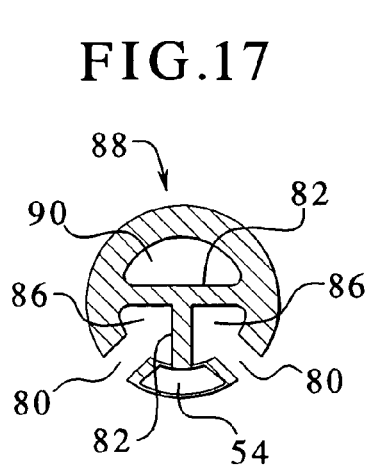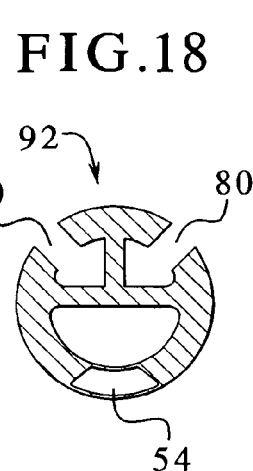

PERITONEAL DIALYSIS CATHETERS

FIELD OF THE INVENTION

The present invention generally relates to catheters, and more specifically, the present invention relates to dual lumen catheters having two fluid flow paths. The catheters can be used for peritoneal dialysis to infuse and remove dialysate simultaneously into and from a patient. The present invention also relates to methods of implanting and using catheters.

BACKGROUND OF THE INVENTION

Kidney failure and reduced kidney function have been treated with dialysis. Dialysis removes waste, toxins, and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis commonly used to treat loss of kidney function. Hemodialysis treatment utilizes the patient's blood to remove waste, toxins, and excess water from the patient. The patient is connected to a hemodialysis machine and the patient's blood is pumped through the machine. Catheters are inserted into the patient's veins and arteries to connect the bloodflow to and from the hemodialysis machine. The waste, toxins, and excess water are removed from the patient's blood and the blood is infused back into the patient. Hemodialysis treatment lasts several hours and is generally performed in a treatment center about three or four times per week.

Peritoneal dialysis utilizes a dialysis solution and dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs due to diffusion and osmosis. The spent dialysate is drained from the patient's peritoneal cavity to remove the waste, toxins, and water from the patient and replaced.

Peritoneal dialysis catheters are used to transfer the fresh dialysate into the peritoneal cavity and remove spent dialysate from the cavity. Typically, a peritoneal catheter is implanted into the peritoneal cavity and remains implanted for an extended period of time. For example, the average catheter may remain implanted for about 18–24 months, but it is not unusual for a catheter to remain indwell for more than 2 years.

There are various types of peritoneal dialysis, including continuous ambulatory peritoneal dialysis (CAPD) and automated peritoneal dialysis. CAPD is a manual dialysis treatment in which the patient connects the implanted catheter to a drain and allows spent dialysate fluid to drain from the peritoneal cavity. The patient then connects to a bag of fresh dialysate and manually infuses the fresh dialysate through the catheter and into the patient's peritoneal cavity. The patient disconnects the catheter from the fresh dialysate bag and allows the dialysate to dwell within the cavity to transfer waste, toxins, and excess water from the patient's bloodstream to the dialysate solution. After the dwell period, the patient repeats the manual dialysis procedure. The patient performs several drain, fill, and dwell cycles during the day, for example, about four times per day. Each treatment cycle typically takes about 3–4 hours. Manual peritoneal dialysis performed by the patient requires quite a lot of time and effort by the patient. The patient is routinely inconvenienced leaving ample opportunity for therapy enhancements to improve patient quality of life.

Automated peritoneal dialysis is similar to continuous peritoneal dialysis in that the dialysis treatment includes a drain, fill, and dwell cycle. However, a dialysis machine automatically performs 3–4 cycles of peritoneal dialysis treatment, typically overnight while the patient sleeps. A dialysis machine is fluidly connected to the implanted catheter. The dialysis machine is also fluidly connected to a source of fresh dialysate, such as a bag of dialysate solution, and to a fluid drain. The dialysis machine pumps spent dialysate from the peritoneal cavity through the catheter to the drain. Then, the dialysis machine pumps fresh dialysate from the dialysate source through the catheter and into the patient's peritoneal cavity. The dialysis machine allows the dialysate to dwell within the cavity to transfer waste, toxins, and excess water from the patient's bloodstream to the dialysate solution. The dialysis machine is computer controlled so that the dialysis treatment occurs automatically when the patient is connected to the dialysis machine, for example, overnight. Several drain, fill, and dwell cycles will occur during the treatment. Also, a last fill is typically used at the end of the automated dialysis treatment so that the patient can disconnect from the dialysis machine and continue daily functions while dialysate remains in the peritoneal cavity. Automated peritoneal dialysis frees the patient from manually performing the drain, dwell, and fill steps, and can improve the patient's dialysis treatment and quality of life.

Various catheters exist for patient implantation to perform peritoneal dialysis. Existing peritoneal catheters include single lumen and dual lumen catheters. A single lumen catheter has a single fluid passageway through the catheter, and a dual lumen catheter has two fluid passageways. Single lumen catheters allow fluid flow in only one direction into or out of the patient at any given moment. Dual lumen catheters allow fluid flow both into and out of the patient at the same time. Because catheters are surgically implanted into patients and because the catheters allow fluids to be infused into and drained from the patients, improvements to catheters and methods of implanting and using catheters can be beneficial.

SUMMARY OF THE INVENTION

The present invention provides new catheters, particularly for continuous flow peritoneal dialysis (CFPD). In CFPD, dialysate flows continuously, i.e. simultaneously, into and out of the patient. The new catheters have two lumens. One lumen allows for fresh dialysate to be infused into the patient, and the other lumen allows for spent dialysate to be removed from the patient. Accordingly, fresh dialysate can flow into the patient simultaneously with spent dialysate flowing out of the patient. It is anticipated that a dialysis machine will be used to automatically perform the dialysis treatment using the new catheters.

The new catheter delivers fresh dialysate into the peritoneal cavity at a location significantly separated from a location at which the catheter removes spent dialysate from the peritoneal cavity. The separation of the patient inflow and outflow locations of the catheter tends to enhance mixing of the dialysate within the peritoneal cavity. Also, as the dialysate flows from the patient inflow location through the peritoneal cavity to the patient outflow location, the dialysate may tend to contact a relatively large area of the peritoneal membrane. A situation in which the dialysate flows directly from the patient inflow location to the patient outflow location on the catheter with minimal contact of the peritoneal membrane, shunting, tends to be avoided. At the patient inflow location, the catheter has fluid openings from the inflow lumen which are directed away from the fluid openings to the patient outflow lumen at the patient outflow location. This direction of the patient inflow fluid openings also tends to enhance dialysate mixing and minimize shunting within the peritoneal cavity.

One catheter according to the present invention extends from a proximal end outside of the patient, upward into the patient and to a preformed bend. The proximal end has openings to the patient inflow and outflow lumens for connection to a dialysis machine, including a dialysate supply and drain. The patient inflow lumen extends from the proximal end to a patient inflow port at the preformed bend. The catheter continues to extend downward from the preformed bend to a distal end inside of the patient's peritoneal cavity. The patient outflow lumen extends from the proximal end to a patient outflow port at the distal end. The distal end of the catheter may have a coiled shape. As implanted into the patient, the preformed bend is positioned in the upper area of the peritoneal cavity and the coiled distal end is positioned in the lower area of the peritoneal cavity. CT Scan and MRI imaging of normal peritoneal dialysis patients lying in supine position (on back) with fluid filled peritoneal cavities shows two distinct pools of fluid. One pool is found in the upper region of the cavity in the vicinity of the liver and spleen. The second pool is located in the lower pelvic region separated from the upper pool by the intestinal mass. This catheter shape was conceived to take advantage of this reality by locating the patient in flow section in the upper pool where fresh dialysate is infused directly. Once infused, the fresh dialysate is forced to filter down through the intestinal mass to the patient outflow section strategically located in the lower pool. This process enhances mixing with spent dialysate and exposes a large area of the peritoneal membrane to "fresher" dialysate for improved toxin and water removal. The catheter shape also assists in maintaining the catheter position within the peritoneal cavity, i.e., the patient inflow preformed bend positioned high in the peritoneum and the patient outflow end positioned low in the peritoneum. This can help reduce or prevent omental adhesion to the catheter due to catheter tip migration which causes catheter fluid flow obstructions.

During dialysis treatment, fluid can flow from the proximal end through the patient inflow lumen, out of the patient inflow port, and into the peritoneal cavity. The fluid inside the cavity contacts the peritoneal membrane, mixes with fluid in the cavity, removes waste, toxins, and water, and flows to the patient outflow port at the distal catheter end. The fluid then flows from the distal end through the patient outflow lumen to the catheter proximal end and is removed from the patient.

Various advantages of the present invention can become apparent upon reading this disclosure including the appended claims with reference to the accompanying drawings. The advantages may be desired, but not necessarily required to practice the present invention.

BRIEF DESCRIPTION OF THE DRAWINGS

FIG. 10 is a longitudinal cross-sectional view of a portion of the catheter of FIG. 1 which transitions from a patient inflow section to a separation section.

FIG. 12 is a longitudinal cross-sectional view of a portion of the catheter of FIG. 1 which transitions from a patient inflow section to a separation section according to the alternate embodiment of FIG. 11.

FIG. 14 is a perspective view of a portion the catheter of FIG. 1 according to FIG. 13.

FIG. 15 is a cross-sectional view along the line XIII–XIII of FIG. 1 showing an alternate fluid port to the patient outflow lumen.

FIG. 16 is a perspective view of a portion of the catheter of FIG. 1 showing the alternate embodiment of the fluid port to the patient inflow lumen of FIG. 15.

FIG. 17 is a cross-sectional view of the catheter of FIG. 1 along the line XIII—XIII showing an alternate cross-section.

FIG. 18 is a cross-sectional view of the catheter of FIG. 1 along the line XIII—XIII showing an alternate cross-section.

FIG. 20 is a plan view of a portion of an alternate catheter according to the principles of the present invention.

DETAILED DESCRIPTION OF PRESENTLY PREFERRED EMBODIMENTS

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

Figure 1:
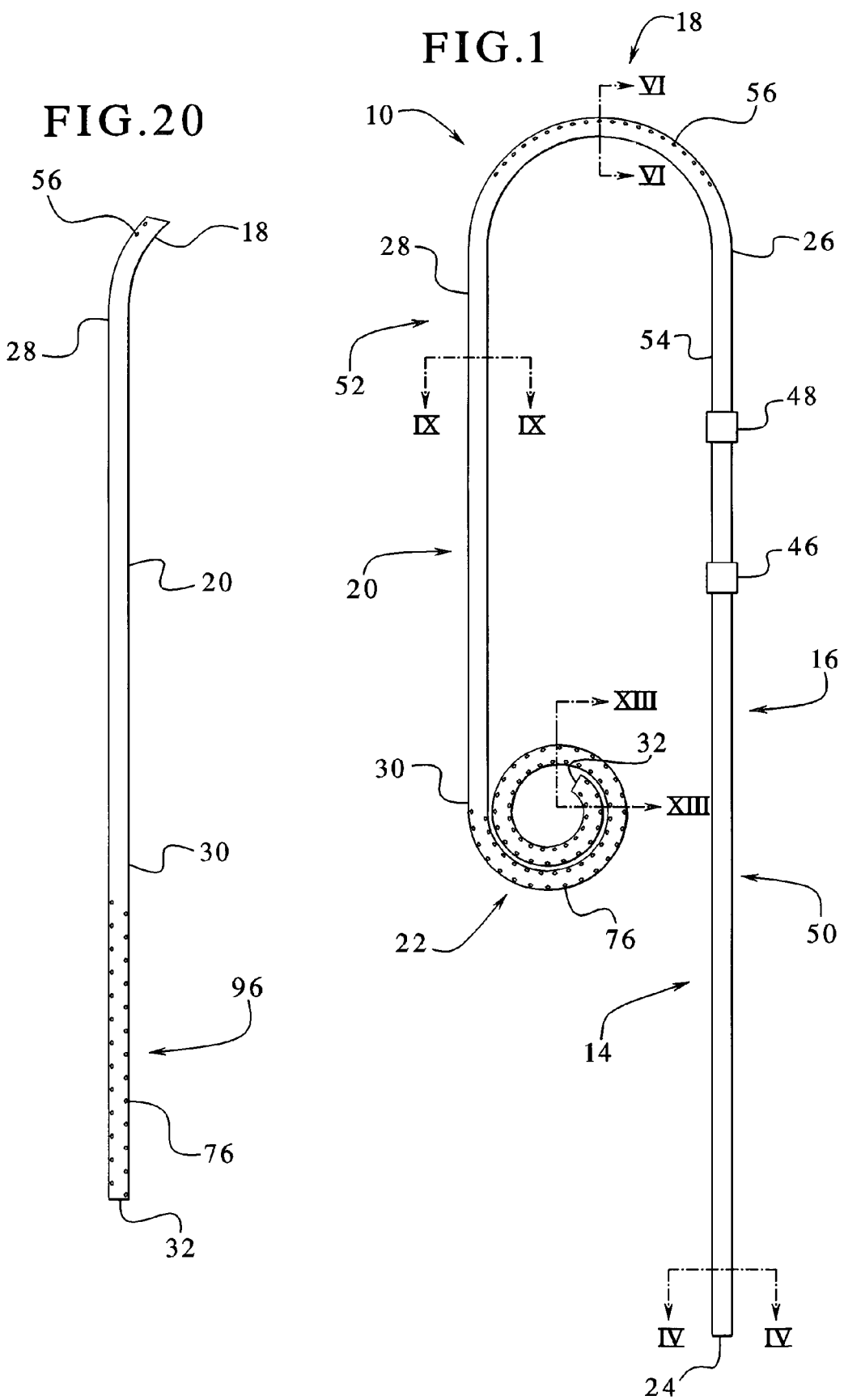
FIG. 1 is a plan view of a catheter according to the principles of the present invention.
Figure 2:
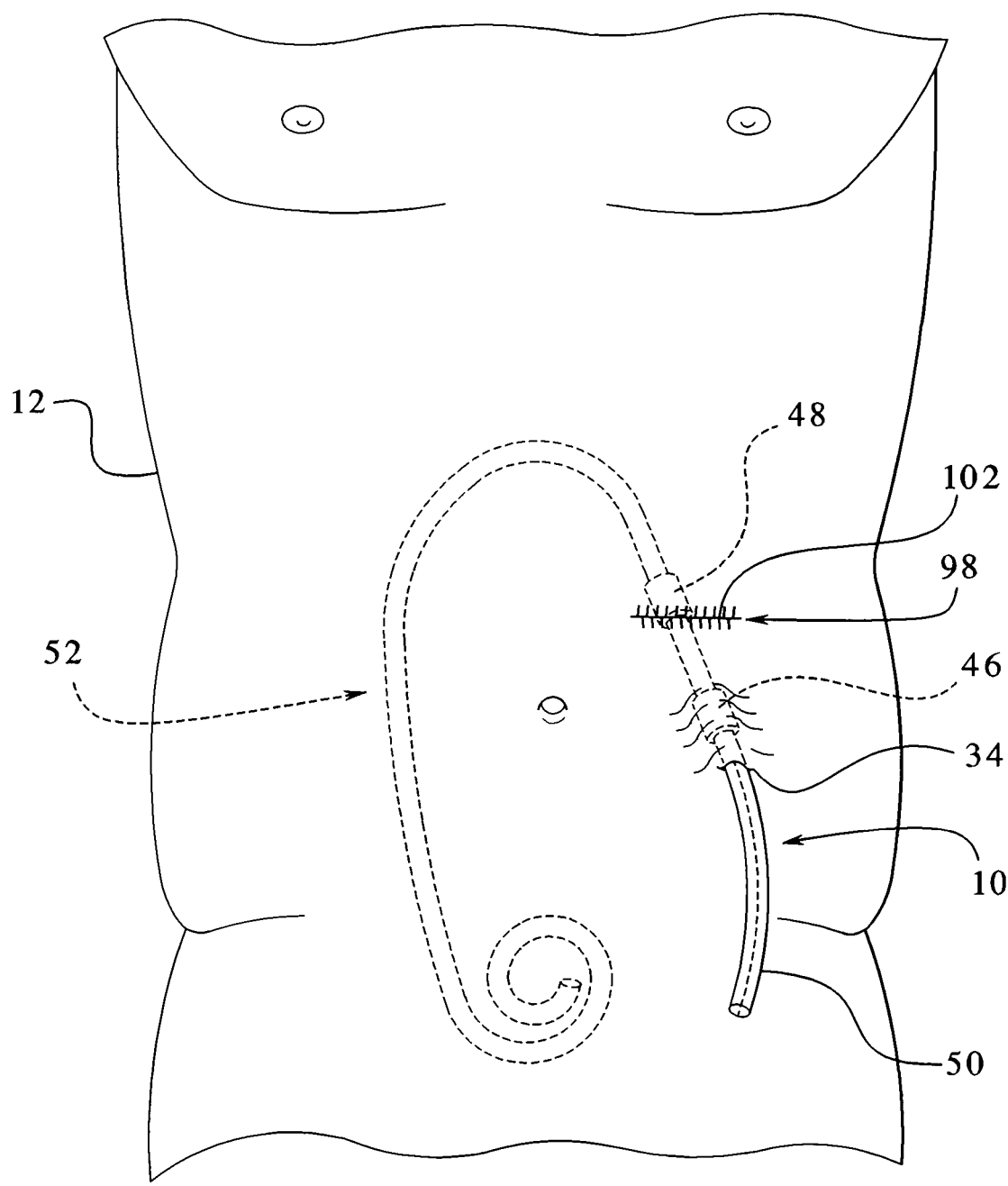
FIG. 2 is a schematic view of the catheter of FIG. 1 implanted into a patient.

A new catheter 10 according to the principles of the present invention is shown by way of example in FIG. 1. The catheter 10 is implanted into a patient's peritoneal cavity for peritoneal dialysis. Referring also to FIG. 2, the catheter 10 is shown partially in phantom implanted into a patient 12.

The catheter 10 allows for dialysate to be infused into and removed out of the peritoneal cavity. Particularly, the catheter 10 allows for continuous flow peritoneal dialysis treatment. Again, continuous flow peritoneal dialysis means that dialysate flows simultaneously into and out of the peritoneal cavity. The catheter 10 can also be used to perform other types of peritoneal dialysis.

The catheter 10 is a dual lumen catheter which has two lumens or fluid flow paths through a flexible tube 14. One lumen provides for fluid to flow from outside the patient, through the catheter 10, and into the patient, i.e. to infuse dialysate into the peritoneal cavity. The second lumen provides for fluid flow in the opposite direction. The second lumen allows fluid to flow from the peritoneal cavity, through the catheter 10, and exit the patient. Continuous flow peritoneal dialysis can be performed on the patient because of the dual lumens in the catheter 10. However, the catheter 10 can be used without simultaneous fluid flow into and out of the patient. For example, the dialysis treatment may be controlled such that fluid flows through only one lumen at any given time. Also, only one lumen could be used, while the other lumen is not used, if desired. Although, the catheter 10 is shown and described as a single tube 14 having multiple lumens, other structures could be used. For example, the catheter 10 could be made of two single lumen tubes joined together along their longitudinal lengths.

The catheter 10 is made of flexible medical grade tubing 14 suitable for implanting inside a patient. Referring to FIG. 1, the catheter 10 can be described as having four main sections, a connection section 16, a patient inflow section 18, an inflow/outflow separation section 20, and a patient outflow section 22. The connection section 16 extends from an external catheter end 24 (proximal end) to a junction 26 with the patient inflow section 18. The patient inflow section 18 is a curved segment which extends from the junction 26 to a junction 28 with the separation section 20. The separation section 20 extends from the junction 28 with the patient inflow section 18 to a junction 30 with the patient outflow section 22. The patient outflow section 22 extends from the junction 30 to an internal catheter end 32 (distal end). The locations of the junctions 26, 28, 30 and the lengths and shapes of the sections 16, 18, 20, 22 can vary depending on the embodiment of the invention.

Referring to FIGS. 1 and 2, the connection section 16 of the catheter 10 provides the function of connecting the catheter 10 to a dialysate supply and removal system, such as an automated continuous flow peritoneal dialysis system (not shown). The external catheter end 24 is positioned external to the patient 12 and is connected to the automated continuous flow peritoneal dialysis system. The catheter 10 has a generally vertical orientation when implanted into the patient 12, with the patient inflow section 18 positioned vertically upward, toward the upper area of the peritoneal cavity. The connection section 16 extends vertically downward and out of the patient 12 at an exit site 34. The separation section 20 also extends vertically downward from the patient inflow section 18. The patient outflow section 22 is positioned downward toward the bottom of the peritoneal cavity.

Figure 3:
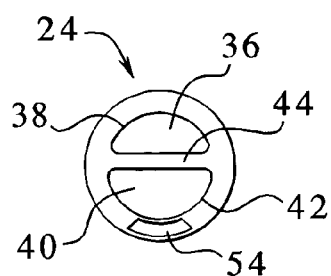
FIG. 3 is an end view of an external catheter end of the catheter of FIG. 1.

An end view of the external catheter end 24 is shown in FIG. 3. A patient inflow lumen 36 allows fluid to flow into the patient from a port 38 at the catheter end 24. A patient outflow lumen 40 allows fluid to flow out of the patient from a port 42 at the catheter end 24. A septum 44 separates the patient inflow and outflow lumens 36, 40 from each other. Accordingly, the patient inflow and outflow lumens 36, 40 allow simultaneous fluid flow into and out of the patient via the dual lumen catheter 10.

Referring to FIGS. 1 and 2, the connection section 16 also provides for anchoring the catheter 10 to the patient. One or more implant cuffs 46, 48 on the connection section 16 anchor the catheter 10 to the patient. The implant cuffs 46, 48 can be polyester felt or other material which allows tissue ingrowth into the cuffs. The catheter 10 is implanted into the patient with the cuff 46 positioned just below the patient's skin and the cuff 48 imbedded in the patient's rectus muscle. The subcutaneous tissue grows into the implant cuffs 46, 48 to anchor the catheter 10 to the patient. When the catheter 10 is implanted inside of a patient, the portion of the catheter 10 from the external catheter end 24 close to the cuff 46 is external to the patient, and is called an external patient portion 50. The remainder of the catheter 10 is implanted inside of the patient and is called an implantable portion 52. As shown in FIG. 1, the implantable portion 52 has a generally non-linear shape, although portions of the implantable portion 52 may be substantially linear.

A radiopaque stripe 54 extends along the length of the catheter 10 with reference to FIGS. 1 and 3. Preferably, the radiopaque stripe 54 extends along the patient outflow lumen 40; however, the radiopaque stripe 54 can be located at any position on the catheter 10 as desired. Under x-ray, the radiopaque stripe 54 shows the position of the catheter 10 inside of the patient.

Figure 4:
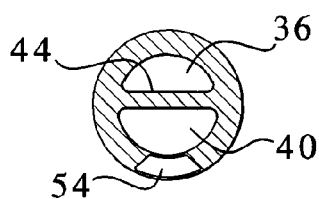
FIG. 4 is a cross-sectional view of the catheter of FIG. 1 along the line IV—IV.

FIG. 4 shows the connection section 16 in cross-section along the section line IV—IV in FIG. 1. The cross-section of the connection section 16 (FIG. 4) is generally consistent along the length of the connection section 16 from the external catheter end 24 to the junction 26. Except, the cuffs 46, 48 are not shown in FIG. 4. Also, the cross-section in the area of the junction 26 may change as the connection section 16 transitions to the patient inflow section 18, depending on the cross-section of the patient inflow section 18.

Figure 5:
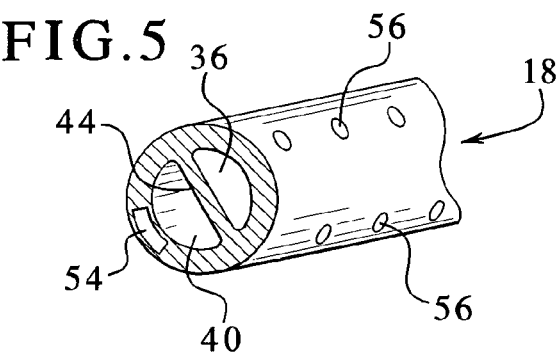
FIG. 5 is a perspective view of a portion the catheter of FIG. 1 showing fluid ports from a patient inflow lumen.

Referring to FIGS. 1 and 5, the patient inflow section 18 has a fluid opening (port) 56 to the patient inflow lumen 36 to allow dialysate to exit the patient inflow lumen 36 and be infused into the peritoneal cavity. The patient inflow section 18 is preformed to a curved shape to form a curved segment. Preferably, the fluid opening 56 is a plurality of round holes through the catheter tube wall along the outer radial surface of the curved inflow segment 18. The curved segment preferably spans an arc of about 180°; however, greater or lesser amounts of curvature can be used. When the catheter 10 is implanted into a patient, the patient inflow section 18 will be positioned generally towards to upper area of the peritoneal cavity, with the remainder of the catheter 10 extending downward.

Figure 6:
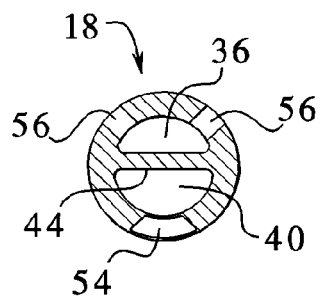
FIG. 6 is a cross-sectional view of the catheter of FIG. 1 along the line VI—VI.

FIG. 6 shows the patient inflow section 18 in cross-section along section line VI—VI of FIG. 1. The cross-section of the patient inflow section 18 is consistent from the connection section 16 to the separation section 20, except for the transitions at the junctions 26, 28, depending the configurations of the lumens 36, 40. The fluid openings 56 in the patient inflow section 18 for the patient inflow lumen 36 are a plurality of round holes. Hole shape and sizes may be varied along the inflow section length in order to create a more uniform flow pattern or a specific flow velocity distribution if so desired. As shown in FIG. 5, there are two rows of evenly spaced holes 56. The two rows of holes 56 are longitudinally offset from each other, however, the offset is not required for proper function of catheter. As shown in FIG. 6, the centerlines of the holes 56 in the two rows of holes form an angle of about 90°, however, other angles could be used. The location of the holes 56 allows for thorough mixing of dialysate within the peritoneal cavity. Referring to FIG. 1, the fluid holes 56 face in a direction away from the patient outflow section 22. Accordingly, the dialysate entering into the peritoneal cavity from the holes 56 in the patient inflow section 18 travels a tortuous path to reach the patient outflow section 22. This tends to enhance dialysate contact on the peritoneal membrane and improve mixing. Improved dialysate contact with the peritoneal membrane and better mixing can improve the dialysis treatment of the patient.

The patient inflow section 18 has been described as having a curved shape. The term curved contemplates structures other than a smooth curve of the tube 14, e.g. a non-linear shape. If one follows along the catheter 10 from the proximal end 24 upward, the patient inflow section 18 reverses the longitudinal direction of the catheter 10 to a downward direction to reach the distal end 32. In addition to having the fluid openings 56, the patient inflow section 18 connects connection section 16 and the separation section 20 together. Accordingly, the curved term contemplates many different shapes, such as an inverted U, an inverted V, a straighter line with right angles at the ends of the lines, and any other structure to connect the connection section 16 to the separation section 20. Also, the patient inflow section 18 is preformed as a curved segment and generally retains its curved shape. Although the tube 14 is flexible, the form-retentive tube 14 will tend to retain its curved shape of the patient inflow section 18 when implanted inside of the patient. The entire tube 14 of the catheter 10 has the flexible, form-retentive characteristic.

Figure 7:
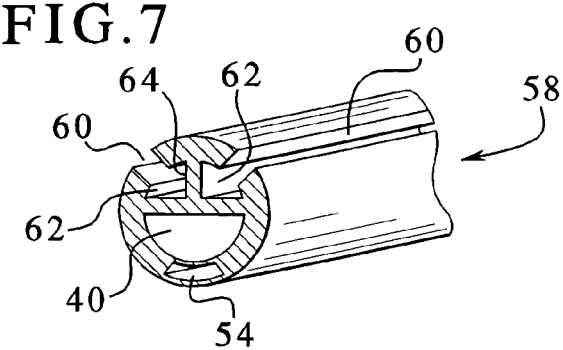
FIG. 7 is a perspective view of a portion of the catheter of FIG. 1 showing an alternate fluid port from the patient inflow lumen.
Figure 8:
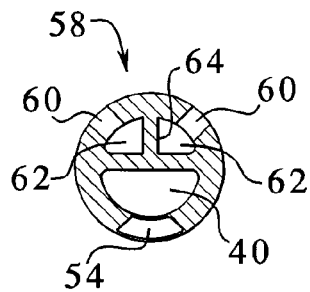
FIG. 8 is a cross-sectional view along the line VI—VI of FIG. 1 showing the alternate embodiment of FIG. 7.

An alternative patient inflow section 58 is shown in FIGS. 7 and 8. Instead of the round holes for the fluid opening 56 in the patient inflow section 18 (FIGS. 5 and 6), the patient inflow section 58 has elongated slots 60 to allow dialysate to flow into the peritoneal cavity. Also, the patient inflow lumen is two patient inflow lumens 62 separated by a septum 64. The septum 64 can have openings to allow fluid flow between both patient inflow lumens 62. The fluid opening 56 can have shapes other than round holes and slots, as desired, for example, elongated holes.

Referring to FIG. 1, the implantable portion 52 of the catheter 10 has a separation section 20. The separation section 20 is a generally straight section of the flexible tube 14 which separates the patient inflow section 18 and the patient outflow section 20 from each other. As described above, when the catheter 10 is implanted into a patient, the patient inflow section 18 is generally positioned at an upper area of the peritoneal cavity to deliver dialysate to the patient. The separation section 20 positions patient outflow section 22 downward toward the lower area of the peritoneal cavity and away from the patient inflow section 18. The separation section 20 allows dialysate flowing into the patient at the patient inflow section 18 to travel a great distance in the peritoneal cavity to reach the patient outflow section 22. The great distance of dialysate fluid flow in the peritoneal cavity also tends to improve the dialysis therapy because the dialysate can contact a greater portion (surface area) of the peritoneal membrane and improved mixing of fresh and spent dialysate can occur.

Figure 9:
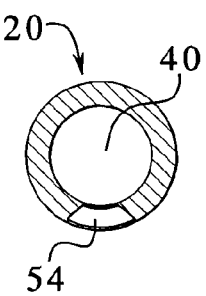
FIG. 9 is a cross-sectional view of the catheter of FIG. 1 along the line IX—IX.

FIG. 9 shows a cross-section of the separation section 20 from the junction 28 with the patient inflow section 18 to the junction 30 with the patient outflow section 22. In this embodiment, the separation section 20 has the patient outflow lumen 40 without the patient inflow lumen 36 because the patient inflow lumen 36 has been terminated. FIG. 10 shows a longitudinal cross-section of the catheter 10 in the area of the junction 28 between the patient inflow section 18 and the separation section 20. The patient inflow lumen 36 terminates at an end 66. The catheter 10 transitions from a dual lumen catheter to a single lumen catheter.

Figure 11:
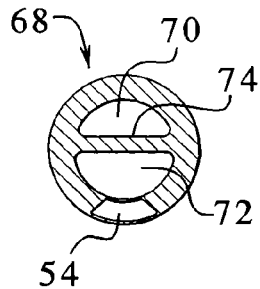
FIG. 11 is a cross-sectional view of the catheter of FIG. 1 along the line IX–IX showing an alternate cross-section.

FIGS. 11 and 12 show cross-sections of an alternative separation section 68. In this embodiment, separation section 68 has both a patient inflow lumen 70 and a patient outflow lumen 72. A septum 74 separates the patient inflow and outflow lumens 70, 72. In this embodiment, the patient inflow lumen 70 may terminate and be dosed at or before the distal catheter end 32.

Figure 13:
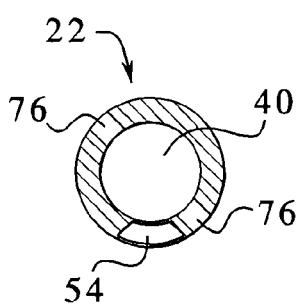
FIG. 13 is a cross-sectional view of the catheter of FIG. 1 along the line XIII—XIII.

The patient outflow section 22 is shown in FIG. 1. The patient outflow section 22 has a preformed, coiled shape. A fluid opening (port) 76 and the open distal end 32 are open to the patient outflow lumen 40 to allow fluid to exit the peritoneal cavity through the catheter 10. Referring also to FIGS. 13 and 14, the fluid opening is preferably a plurality of holes 76 generally all around the exterior of the tube 14 from the junction 30 to the distal end 32. The patient outflow section 22 with the fluid opening 76 is spaced a great distance from the patient inflow section 18 and the fluid opening 56. Accordingly, dialysate fluid must flow from the patient inflow section 18–positioned in the upper area of the peritoneal cavity—a great distance to the patient outflow section 22—positioned in the lower area of the peritoneal cavity. The inflow and outflow of dialysate fluid through the catheter 10 can occur simultaneously.

FIGS. 15 and 16 show an alternative patient outflow section 78. In this embodiment, instead of holes 76, the fluid opening is a plurality of elongated slots 80. Several septums 82 are connected together and hold the outer tube portions 84 together. The patient outflow lumen is partitioned into several patient outflow lumens 86 by the septums 82. The septums 82 can have openings to allow fluid flow between any of the patient outflow lumens 86. Of course, the fluid opening 76 in the patient outflow section could have shapes other than holes and slots as desired.

Figure 19:
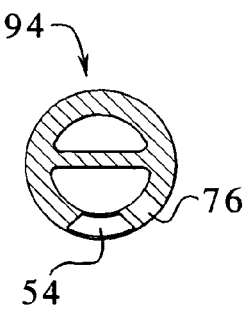
FIG. 19 is a cross-sectional view of the catheter of FIG. 1 along the line XIII—XIII showing an alternate cross-section.

FIGS. 17–19 show additional alternate cross-sections of the patient outflow section 22. In FIG. 17, the patient outflow section 88 has slots 80 on only the side of the tube having the radiopaque stripe 54. Lumen 90 can be part of the patient outflow lumen by carrying fluid out of the patient from an open distal end 32 and/or from fluid openings through the septums 82 to the lumens 86. The lumen 90 could be part of the patient inflow lumen 36, but would have a closed end at or prior to the distal end 32. The patient outflow section 88 of FIG. 17 may have greater structural strength around lumen 90 because there are no slots opposite the radiopaque stripe 54. Accordingly, the lumen 90 may provide greater containment of a stiffening stylet inserted into the lumen 90 during implantation of the catheter 10. The patient outflow section 92 of FIG. 18 is similar to the patient outflow section 88 of FIG. 17. Except, the slots 80 in the FIG. 18 embodiment are on the side of the tube opposite the radiopaque stripe. The patient outflow section 94 of FIG. 19 is similar to the patient outflow section 88 of FIG. 17. Except, holes 76 replace the slots 80.

FIG. 20 shows an alternative embodiment of the catheter 10. In this embodiment, the catheter 10 is generally the same as previously described embodiments, except for the patient outflow section 22. The flexible patient outflow section 96 has a substantially straight shape rather than the coiled shape of the patient outflow section 22 shown in FIG. 1. The patient outflow section 96 has a port, such as a plurality of holes 76 or slots 80, for the patient outflow lumen 40. The cross-sections of the patient outflow sections shown in FIGS. 13, 15, and 17–19 are also applicable to the patient outflow section 96 of FIG. 20.

Implantation of the catheter 10 into a patient will now be described. Generally, the catheter 10 can be implanted by accepted catheter implantation methods, including open surgical dissection, peritoneoscopic, and percutaneous, for example, with modifications due to the new catheters of the present invention. Because the open surgical dissection method is the most commonly used implantation method for existing peritoneal dialysis catheters, an open surgical dissection implantation method for the catheter 10 will be described. This disclosure of the invention is not a medical text and, thus, the procedural steps described below do not constitute a complete formal medical procedure. Medical professionals should determine and apply all appropriate procedures.

I. Patient Preparation

Preparation for catheter placement should follow accepted hospital procedures for general abdominal surgery.

1. Empty the patient's bowel and bladder. An enema should be used, if necessary.

Figure 21:
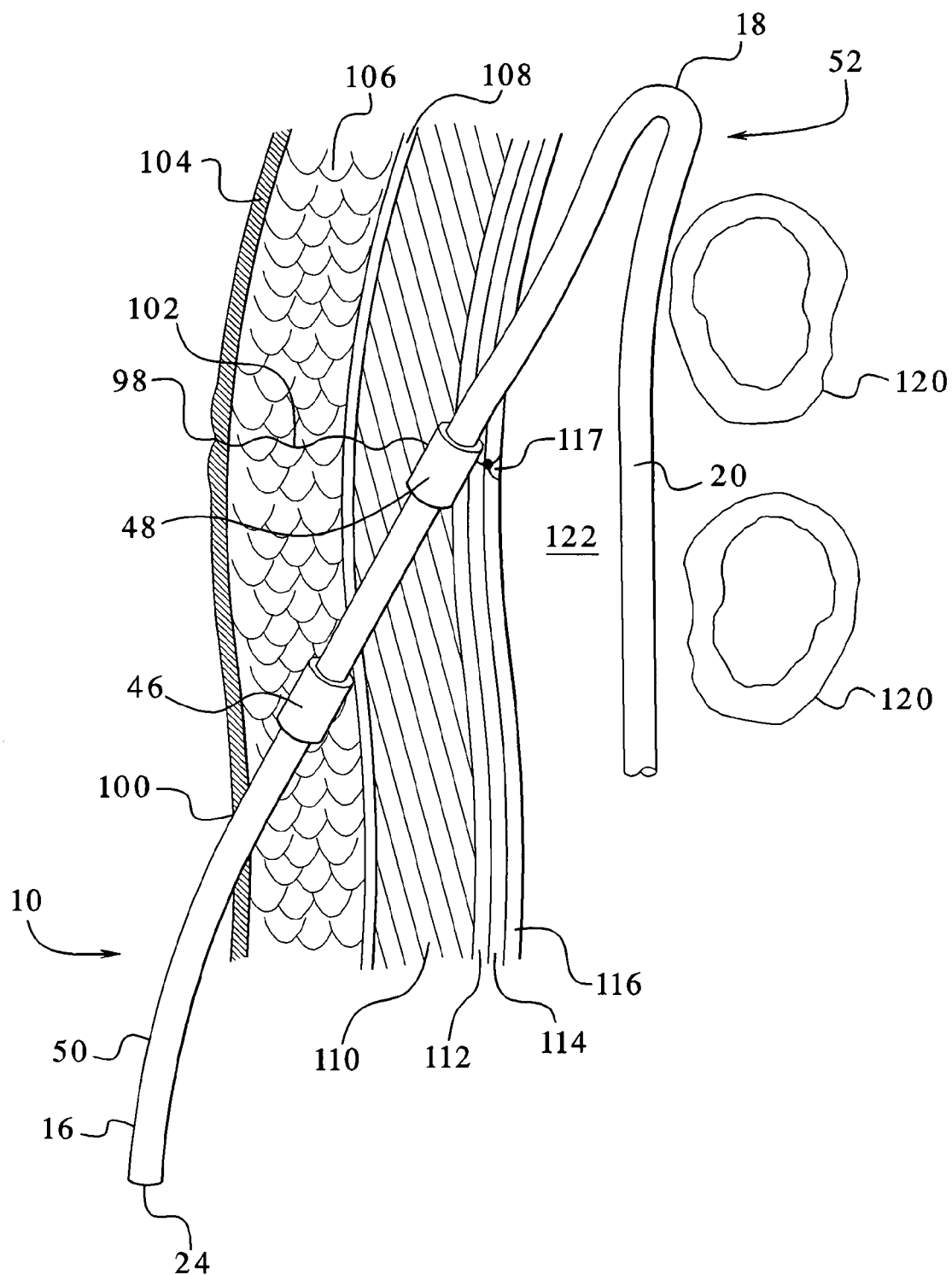
FIG. 21 is a schematic partial cross-sectional view of a patient showing the catheter of FIG. 1 implanted in the patient.

2. Shave the insertion area and mark entrance and exit locations with a sterile ink pen. Referring to FIG. 21, the entrance site 98 will be located approximately 3–6 cm directly above the exit site 100, or above and slightly to the side of the exit site 100. These locations of the entrance and exit sites 98, 100 provide for the external patient portion 50 of the catheter 10 to be directed downward and the implantable portion 52 to point upward to the patient inflow section 18.

3. Prepare the sterile field. After a Betadine scrub, the entrance and exit markings may need to be reapplied.

4. Anesthetize the area locally where the initial incision, tunnel and subsequent skin puncture will be made. Avoid general anesthesia whenever possible.

5. Patient is now ready for implantation of the catheter 10.

II. Catheter Implantation

1. A 3–4 cm transverse incision 102 is made through the skin 104 and subcutaneous tissue 106. The transverse incision 102 is continued down through the anterior rectus sheath 108.

2. The rectus muscle fibers 110 are separated to expose the posterior rectus sheath 112.

3. An incision is made through the posterior rectus sheath 112, transversalis fascia 114, and parietal peritoneum 116 no larger than necessary to introduce the catheter 10.

4. A purse-string suture 117 is placed around the incision to help seal after catheter insertion.

5. The catheter 10 is placed in a sterile saline bath while compressing the cuffs 46, 48 to remove any entrapped air.

Figure 22:
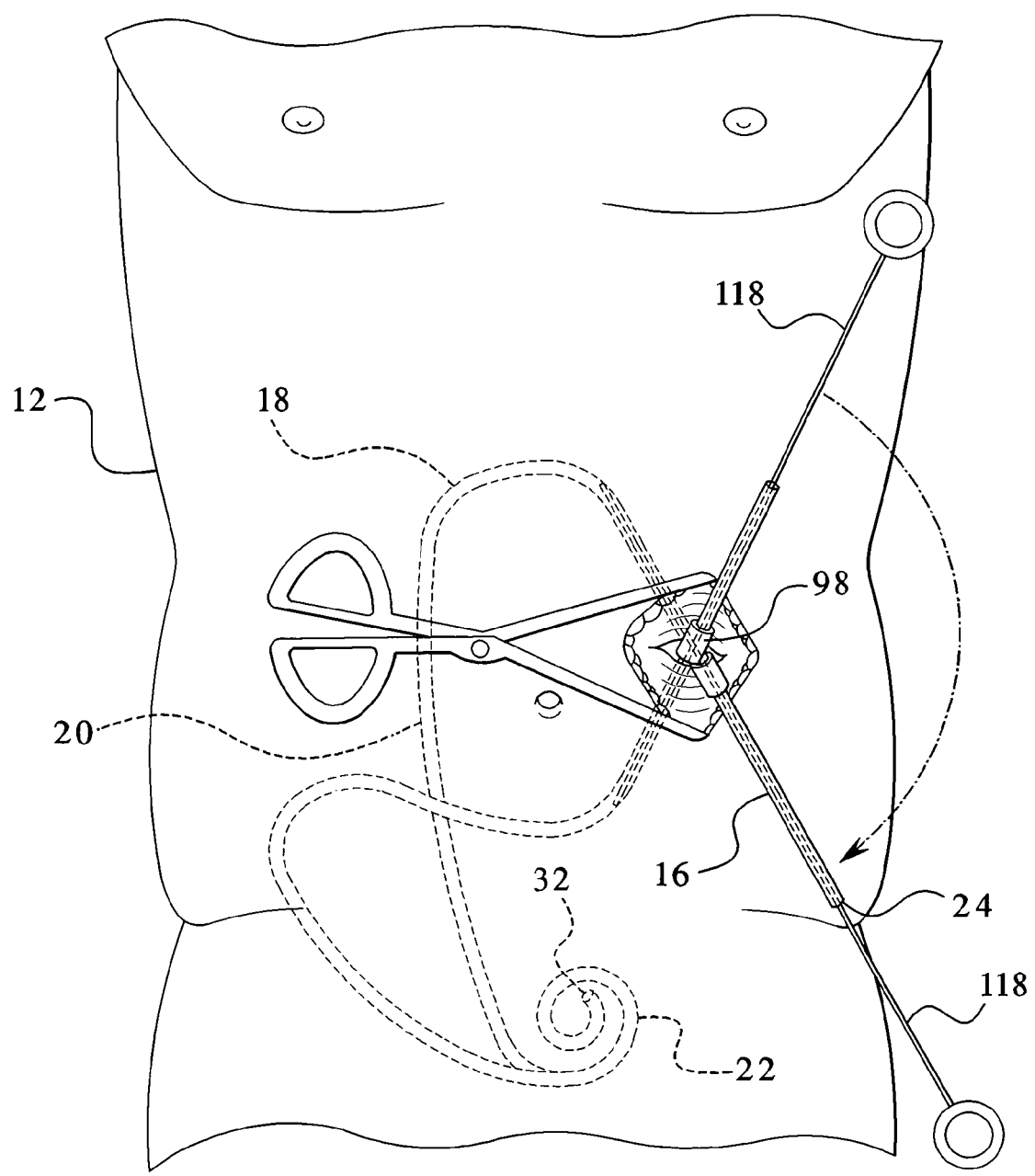
FIG. 22 is a schematic view showing the catheter of FIG. 1 being implanted into a patient.

6. Referring to FIGS. 21 and 22, a stiffening stylet 118 is inserted into the patient outflow lumen 40 (lumen identified by radiopaque stripe) of the catheter 10. The stylet 118 stiffens the catheter 10 and straightens the curved patient inflow section 18 and the coiled patient outflow section 22 for easier insertion. The stylet 118 should fall at least 1 cm short of the distal end 32 of the catheter 10 to prevent perforation of the bowel 120 or other intraperitoneal injury.

7. As shown in FIG. 22, the catheter 10 is initially directed downward toward the lower pelvis with the stylet 118 pointing downward. With the coiled patient outflow section 22 embodiment, once the catheter tip (distal end 32) is deep in the pelvic cavity the stylet 118 is slowly removed approximately 20 cm while simultaneously advancing the catheter 10 deeper to allow the coil to reform its coiled shape and remain low in the pelvis.

8. Once the catheter tip (distal end 32), coiled or straight embodiments, is properly located low in the pelvis, the stylet 118 is removed another 10 cm while advancing the catheter 10 inward by the same amount. At this point the stylet 118 should remain fixed while advancing the catheter 10 all the way into the peritoneum 122 until the distal cuff 48 is seated firmly in the rectus muscle 110 but not protruding into the peritoneum 122.

9. The portion of the stylet 118 and catheter 10 external to the patient is rotated approximately 135° downward with the portion of the stylet 118 and catheter 10 inside of the patient rotated upward as shown in FIG. 22 to force the patient inflow section 18 into the upper portion of the abdomen near the liver. During this step the catheter 10 should be kept as close to the abdominal wall as possible. Ideal placement would result in the catheter 10 lying in the area between the intestinal mass (bowels 120) and the posterior abdominal wall as shown in FIG. 21.

10. The purse-string suture 117 is firmly cinched around the catheter 10. An additional suture can be added to secure the cuff 48 to the rectus muscle 110 if desired.

III. Subcutaneous Tunnel

1. A tunneling tool is inserted into one of the catheter lumens 36, 40.

2. A small scalpel puncture is made at the premarked exit site 100 location which is directly below or below and slightly to one side of the entrance site 98 location.

3. Referring to FIG. 21, the tunneling tool with catheter 10 attached is advanced from the original entrance site incision 102, under the skin 104 and out the scalpel puncture at the exit site 100 forming a straight, stress-free subcutaneous tunnel. The catheter 10 is pulled through the tunnel until the catheter 10 is straightened and the proximal cuff 46 is approximately 2 cm below the skin surface.

IV. Finish Procedure

1. An adapter is attached to the proximal end 24 of the catheter 10 and catheter flow is assessed by infusing and draining saline solution through both lumens 36, 40.

2. Once the fluid flow function is validated, the entrance site incision 102 is closed. Suturing of exit site 100 is not recommended.

3. The catheter 10 is secured to the skin and the exit wound is dressed appropriately.

Dialysis may begin as early as required, but recommended no sooner than 2 weeks.

The catheter 10 and the implantation method provides for an unstressed, straight tunnel through the patient's tissue into the peritoneal cavity 122. Also, the exit site 100 is directed downward so the external patient portion 50 of the catheter 10 is positioned in a downward direction. The catheter 10 can have a close implant cuff spacing (small distance between implant cuffs 46, 48). Accordingly, only a small length of catheter tubing between the implant cuffs 46, 48 will be positioned within the patient's abdominal wall tissue.

While the presently preferred embodiments have been illustrated and described, numerous changes and modifications can be made without significantly departing from the spirit and scope of this invention. Therefore, the inventors intend that such changes and modifications are covered by the appended claims.

The invention is claimed as:

1. A dialysis catheter comprising:
   a connection section having an inflow port to a patient inflow lumen, and an outflow port to a patient outflow lumen, the lumens separated by an internal septum;
   a patient inflow section extending from the connection section and having a patient inflow opening formed thereon and in fluid communication with the patient inflow lumen;
   a separation section extending from the patient inflow section, which is substantially straight when in an unstressed condition; and
   a patient outflow section extending from the separation section, having a patient outflow opening in fluid communication with the patient outflow lumen, and wherein when the catheter is in a substantially unstressed condition, (i) the connection section is substantially straight and (ii) the patient inflow section is curved.

2. The dialysis catheter of claim 1, wherein the patient outflow section is coiled.

3. The dialysis catheter of claim 1, wherein the patient outflow section is substantially straight.

4. The dialysis catheter of claim 1, wherein the patient inflow section is an uppermost portion of an implantable portion of the catheter and the patient outflow section is a lowermost portion of the implantable portion of the catheter.

5. The dialysis catheter of claim 1, wherein the connection section, patient inflow section, separation section, and patient outflow section further comprise a flexible tube having an internal septum between the patient inflow and outflow lumens.

6. The dialysis catheter of claim 1, wherein the patient inflow section has a curved shape.

7. The dialysis catheter of claim 1, wherein the patient inflow opening in fluid communication with the patient inflow lumen is in a direction away from the patient outflow opening to the patient outflow lumen.

8. The dialysis catheter of claim 1, wherein the catheter comprises a single tube having the patient inflow and outflow lumens, and wherein the tube transitions from having both the patient inflow and outflow lumens to having only the patient outflow lumen at a location between the patient inflow section and a distal catheter end.

9. A dialysis catheter comprising:
a connection section substantially straight when in an unstressed condition;
a patient inflow section having a non-linear shape when in an unstressed condition and having a patient inflow opening formed thereon, the inflow section extending from the connection section;
a separation section extending from the patient inflow section, the separation section having a substantially straight shape when in an unstressed condition;
a patient outflow section extending from the separation section;
a patient inflow lumen extending from the connection section to the patient inflow section; and
a patient outflow lumen extending from the connection section to the patient outflow section the patient inflow and outflow lumens separated by an internal septum.

10. The dialysis catheter of claim 9, wherein the patient outflow section has a coiled shape.

11. The dialysis catheter of claim 9, wherein the patient inflow section has a curved shape of about 180°.

12. A peritoneal dialysis catheter having first and second lumens, comprising:
a dialysis machine connection section having fluid ports in fluid communication with the first and second lumens the first and second lumens separated by an internal septum;
a section having a non-linear shape when in an unstressed condition, the non-linear section extending from the connection section and having a fluid opening formed thereon and in fluid communication with the first lumen;
a separation section extending from the non-linear section, the separation section preformed to be substantially straight when in an unstressed condition; and
a distal end section extending from the separation section and having a fluid opening formed thereon and in fluid communication with the second lumen.

13. The peritoneal dialysis catheter of claim 12, wherein the first lumen is a patient inflow lumen and the second lumen is a patient outflow lumen.

14. The peritoneal dialysis catheter of claim 12, wherein the non-linear section has a curved shape and the fluid port in the non-linear section is pointed in a direction opposite the fluid port in the distal end section.

15. A dialysis system, comprising:
a fluid flow system capable of conveying fluid to and from a patient; and
a catheter having first and second lumens fluidly connected to the fluid flow system, the first and second lumens separated by an internal septum, the catheter having a tube extending from an external proximal end to a single implantable free distal end, the tube having patient inflow and outflow portions spaced from each other along the tube, the patient in-flow portion having a preformed non-linear shape and a patient inflow opening formed thereon, and wherein the patient inflow portion is connected to the patient outflow portion by a substantially straight portion when in an unstressed condition.

16. The dialysis system of claim 15, wherein the fluid flow system is a continuous flow dialysis system.

17. The dialysis system of claim 15, wherein the fluid flow system is an automated continuous flow peritoneal dialysis system.

18. The dialysis system of claim 15, wherein the tube is so positioned and arranged when in use in a peritoneal cavity that fluid exits the catheter from the patient inflow portion to an upper area of the peritoneal cavity, flows across a portion of the peritoneal cavity, and re-enters the catheter at the patient outflow portion at a lower area of the peritoneal cavity.

19. The dialysis system of claim 15, wherein the patient inflow portion is fluidly connected to the first lumen, and the patient outflow portion is fluidly connected to the second lumen, and wherein when the dialysis system is in use, fluid simultaneously flows in opposite directions through the first and second lumens.

20. The dialysis system of claim 15, wherein the patient inflow and outflow portions are located at opposite upper and lower portions of an implantable portion of the catheter.

21. The dialysis system of claim 15, wherein the patient inflow portion has a generally arcuate shape.

22. The dialysis system of claim 15, wherein the tube is a single tube having the first and second lumens.

23. A peritoneal dialysis system, comprising:
a fluid flow system capable of conveying fluid to and from a patient; and
a catheter having first and second lumens fluidly connected to the fluid flow system, the first and second lumens separated by an internal septum, the catheter further comprising:
a system connection portion fluidly connected to the fluid flow system and so positioned and arranged when in use to extend from outside of the patient upward into a peritoneal cavity of the patient;
an upper preformed non-linear portion fluidly connected to the system connection portion and having a fluid opening formed thereon and fluidly connecting the first lumen to the peritoneal cavity; and
a lower portion fluidly connected to and extending downward from the upper non-linear portion and having a fluid opening formed thereon and fluidly connecting the second lumen to the peritoneal cavity, wherein the upper preformed non-linear portion is connected to the lower portion by a substantially straight portion when in an unstressed condition.

24. The peritoneal dialysis system of claim 23, wherein the fluid flow system is a continuous flow dialysis system.

25. The peritoneal dialysis system of claim 23, wherein the fluid flow system is an automated continuous flow peritoneal dialysis system.

26. The peritoneal dialysis system of claim 23, wherein the catheter and the fluid openings to the first and second lumens are so positioned and arranged when in use in a peritoneal cavity that fluid flows out of the first lumen at an upper area of the peritoneal cavity and subsequently into the second lumen at an lower area of the peritoneal cavity.

27. The peritoneal dialysis system of claim 23, wherein the catheter further comprises a single tube having the first and second lumens.

28. The peritoneal dialysis system of claim 23, wherein the upper preformed non-linear portion is a patient inflow portion, and the lower portion is a patient outflow portion, and wherein when the dialysis system is in use, fluid simultaneously flows in opposite directions through the first and second lumens.

29. The peritoneal dialysis system of claim 23, wherein the upper preformed non-linear portion has a non-linear shape in a section having the fluid opening to the first lumen.

30. The peritoneal dialysis system of claim 23, wherein the upper preformed non-linear portion has a generally inverted U shape.

31. A peritoneal dialysis catheter, comprising:
a tube having first and second lumens separated by an internal septum, the tube extending from an external proximal end to a single implantable free distal end; and
patient inflow and outflow portions spaced from each other along the tube, the patient in-flow portion having a preformed non-linear shape and a patient inflow opening formed thereon, and wherein the patient inflow portion is connected to the patient outflow portion by a substantially straight portion when in an unstressed condition.

32. The peritoneal dialysis catheter of claim 31, wherein the tube is so positioned and arranged when in use in a peritoneal cavity that fluid exits the catheter from the patient inflow portion to an upper area of the peritoneal cavity, flows across a portion of the peritoneal cavity, and re-enters the catheter at the patient outflow portion at a lower area of the peritoneal cavity.

33. The peritoneal dialysis catheter of claim 31, wherein the patient inflow portion is fluidly connected to the first lumen, and the patient outflow portion is fluidly connected to the second lumen, and wherein when the catheter is in use, fluid simultaneously flows in opposite directions through the first and second lumens.

34. The peritoneal dialysis catheter of claim 31, wherein the patient inflow and outflow portions are located at opposite upper and lower portions of an implantable portion of the catheter.

35. The peritoneal dialysis catheter of claim 31, wherein the tube is a single tube having the first and second lumens.

36. A peritoneal dialysis catheter for use with a fluid flow system for conveying fluid to a peritoneal cavity of a patient, the catheter comprising:
first and second lumens separated by an internal septum;
a system connection portion which fluidly connects the first and second lumens to the fluid flow system, the system connection portion so positioned and arranged when in use to extend from outside of the patient upward into the peritoneal cavity of the patient;
an upper preformed non-linear portion fluidly connected to the system connection portion and having a fluid opening formed thereon and fluidly connecting the first lumen to the peritoneal cavity; and
a lower portion fluidly connected to and extending downward from the upper non-linear portion and having a fluid opening formed thereon and fluidly connecting the second lumen to the peritoneal cavity, wherein the upper preformed non-linear portion is connected to the lower portion by a substantially straight portion when in an unstressed condition.

37. The peritoneal dialysis catheter of claim 36, wherein the catheter and the fluid openings in fluid communication with the first and second lumens are so positioned and arranged when in use in a peritoneal cavity that fluid flows out of the first lumen at an upper area of the peritoneal cavity and subsequently into the second lumen at an lower area of the peritoneal cavity.

38. The peritoneal dialysis catheter of claim 36, wherein the catheter further comprises a single tube having the first and second lumens.

39. The peritoneal dialysis catheter of claim 36, wherein the upper preformed non-linear portion is a patient inflow portion, and the lower portion is a patient outflow portion, and wherein when the peritoneal dialysis catheter is in use, fluid simultaneously flows in opposite directions through the first and second lumens.

40. A peritoneal dialysis catheter for use in a peritoneal cavity of a patient, the catheter comprising:
an implantable portion;
a first lumen extending through at least a portion of the implantable portion;
a first fluid opening in fluid communication with the first lumen and formed on a first location along the implantable portion;
a second lumen having a different length than the first lumen and extending through at least a portion of the implantable portion the first and second lumens separated by an internal septum; and
a second fluid opening in fluid communication with the second lumen and formed on a second location along the implantable portion different from the first location of the first fluid opening at least one of the first and second location having a curve when in an unstressed condition;
wherein the first and second lumens are so positioned and arranged when the implantable portion is implanted in the peritoneal cavity that the first lumen is side-by-side the second lumen and the fluid openings are at generally opposite portions of the peritoneal cavity.

41. The peritoneal dialysis catheter of claim 40, wherein the catheter is so constructed and arranged that fluid can flow simultaneously through the first and second lumens.

42. The peritoneal dialysis catheter of claim 40, wherein the catheter is so constructed and arranged that fluid can flow simultaneously in opposite directions through the first and second lumens.

43. The peritoneal dialysis catheter of claim 40, wherein the catheter further comprises a single tube having the first and second lumens.

44. The peritoneal dialysis catheter of claim 40, wherein the catheter is so positioned and arranged when in use in a peritoneal cavity that fluid flows across a substantial portion of the peritoneal cavity from the first lumen to the second lumen.

* * * * *